(12) United States Patent
Taylor et al.

(10) Patent No.: US 7,722,654 B2
(45) Date of Patent: May 25, 2010

(54) SPINAL IMPLANTS WITH MULTI-AXIAL ANCHOR ASSEMBLY AND METHODS

(75) Inventors: Harold Sparr Taylor, Memphis, TN (US); Terrance Strohkirch, Cordova, TN (US); Matthew M. Morrison, Cordova, TN (US); Michael Veldman, Olive Branch, MS (US)

(73) Assignee: Warsaw Orthopedic, Inc.

( * ) Notice: Subject to any disclaimer, the term of this patent is extended or adjusted under 35 U.S.C. 154(b) by 631 days.

(21) Appl. No.: 10/958,977

(22) Filed: Oct. 5, 2004

(65) Prior Publication Data

US 2006/0074419 A1 Apr. 6, 2006

(51) Int. Cl.
*A61B 17/58* (2006.01)
(52) U.S. Cl. ...................... 606/287; 606/301
(58) Field of Classification Search .............. 606/69, 606/70, 71, 73, 264–278, 280, 286–297, 606/300–331
See application file for complete search history.

(56) References Cited

U.S. PATENT DOCUMENTS

| | | | |
|---|---|---|---|
| 4,569,338 A | 2/1986 | Edwards | |
| 4,729,703 A | 3/1988 | Sato | |
| 4,827,918 A | 5/1989 | Olerud | |
| 4,913,134 A * | 4/1990 | Luque | 606/61 |
| 5,047,029 A | 9/1991 | Aebi et al. | |
| 5,053,034 A | 10/1991 | Olerud | |
| 5,176,680 A | 1/1993 | Vignaud et al. | |
| 5,234,431 A | 8/1993 | Keller | |
| 5,254,118 A | 10/1993 | Mirkovic | |
| 5,360,431 A * | 11/1994 | Puno et al. | 606/72 |
| 5,474,555 A | 12/1995 | Puno et al. | |
| 5,499,983 A * | 3/1996 | Hughes | 606/267 |
| 5,527,314 A | 6/1996 | Brumfield et al. | |
| 5,527,315 A | 6/1996 | Jeanson et al. | |
| 5,534,002 A | 7/1996 | Brumfield et al. | |
| 5,540,690 A * | 7/1996 | Miller et al. | 606/61 |
| 5,545,166 A | 8/1996 | Howland | |
| 5,562,662 A | 10/1996 | Brumfield | |
| 5,569,247 A | 10/1996 | Morrison | |
| 5,591,166 A | 1/1997 | Bernhardt et al. | |
| 5,607,426 A * | 3/1997 | Ralph et al. | 606/61 |

(Continued)

FOREIGN PATENT DOCUMENTS

DE 19829699 1/2000

(Continued)

OTHER PUBLICATIONS

"Along". The Merriam-Webster Online Dictionary, [Online ], [retrieved on Apr. 25, 2007]. Retreived from the internet URL<URL:http://www.m-w.com/cgi-bin/dictionary>.*

(Continued)

*Primary Examiner*—Eduardo C Robert
*Assistant Examiner*—Mary Hoffman

(57) ABSTRACT

System and methods are provided that include a plate member engageable to the spinal column with an anchor assembly. The anchor assembly includes a coupling member having a post extending through at least one opening of the plate member and an anchor member pivotally captured in a receiver member of the coupling member below a lower surface of the plate member. A locking member secures the plate member to the coupling member.

32 Claims, 11 Drawing Sheets

U.S. PATENT DOCUMENTS

| | | | |
|---|---|---|---|
| 5,628,740 A | 5/1997 | Mullane | |
| 5,643,263 A | 7/1997 | Simonson | |
| 5,643,265 A * | 7/1997 | Errico et al. | 606/70 |
| 5,725,528 A | 3/1998 | Errico et al. | |
| 5,735,851 A | 4/1998 | Errico et al. | |
| 5,800,435 A | 9/1998 | Errico et al. | |
| 5,885,285 A | 3/1999 | Simonson | |
| 5,904,683 A | 5/1999 | Pohndorf et al. | |
| 5,938,663 A | 8/1999 | Petreto | |
| 5,947,967 A | 9/1999 | Barker | |
| 6,004,349 A | 12/1999 | Jackson | |
| 6,010,504 A | 1/2000 | Rogozinski | |
| 6,050,997 A | 4/2000 | Mullane | |
| 6,132,432 A | 10/2000 | Richelsoph | |
| 6,183,473 B1 | 2/2001 | Ashman | |
| 6,187,005 B1 | 2/2001 | Brace et al. | |
| 6,210,413 B1 | 4/2001 | Justis et al. | |
| 6,248,107 B1 | 6/2001 | Foley | |
| 6,267,765 B1 | 7/2001 | Taylor et al. | |
| 6,280,442 B1 * | 8/2001 | Barker et al. | 606/60 |
| 6,302,888 B1 | 10/2001 | Mellinger et al. | |
| 6,315,779 B1 | 11/2001 | Morrison et al. | |
| 6,352,537 B1 | 3/2002 | Strnad | |
| 6,355,038 B1 | 3/2002 | Pisharodi | |
| 6,478,798 B1 | 11/2002 | Howland | |
| 6,520,962 B1 | 2/2003 | Taylor et al. | |
| 6,524,315 B1 * | 2/2003 | Selvitelli et al. | 606/70 |
| 6,547,790 B2 | 4/2003 | Harkey, III et al. | |
| 6,562,038 B1 | 5/2003 | Morrison | |
| 6,565,567 B1 | 5/2003 | Haider | |
| 6,626,906 B1 | 9/2003 | Young | |
| 6,685,705 B1 | 2/2004 | Taylor et al. | |
| 6,730,093 B2 | 5/2004 | Saint Martin | |
| 6,755,829 B1 | 6/2004 | Bono et al. | |
| 6,770,075 B2 | 8/2004 | Howland | |
| 7,022,122 B2 | 4/2006 | Amrein et al. | |
| 7,572,280 B2 | 8/2009 | Dickinson et al. | |
| 2003/0073996 A1 * | 4/2003 | Doubler et al. | 606/61 |
| 2003/0125741 A1 | 7/2003 | Biedermann et al. | |
| 2004/0116929 A1 | 6/2004 | Barker et al. | |
| 2004/0158247 A1 | 8/2004 | Sitiso et al. | |
| 2005/0177154 A1 | 8/2005 | Moumene et al. | |
| 2005/0261687 A1 | 11/2005 | Garamszegi et al. | |
| 2005/0277923 A1 | 12/2005 | Sweeney | |
| 2005/0277928 A1 | 12/2005 | Boschert | |
| 2006/0084980 A1 | 4/2006 | Melkent et al. | |
| 2006/0084989 A1 | 4/2006 | Dickinson et al. | |
| 2006/0264933 A1 | 11/2006 | Baker et al. | |
| 2007/0016188 A1 | 1/2007 | Boehm et al. | |

FOREIGN PATENT DOCUMENTS

| | | |
|---|---|---|
| DE | 202004009073 | 8/2004 |
| EP | 0947174 | 10/1999 |

OTHER PUBLICATIONS

TiMX Comprehensive Low Back System, DePuy AcroMed, © 1999.
Pass® Deformity System, Encore Surgical, © Jan. 2002.
Spine Internal Fixation Device, Encore Surgical, © Jan. 2002.

* cited by examiner

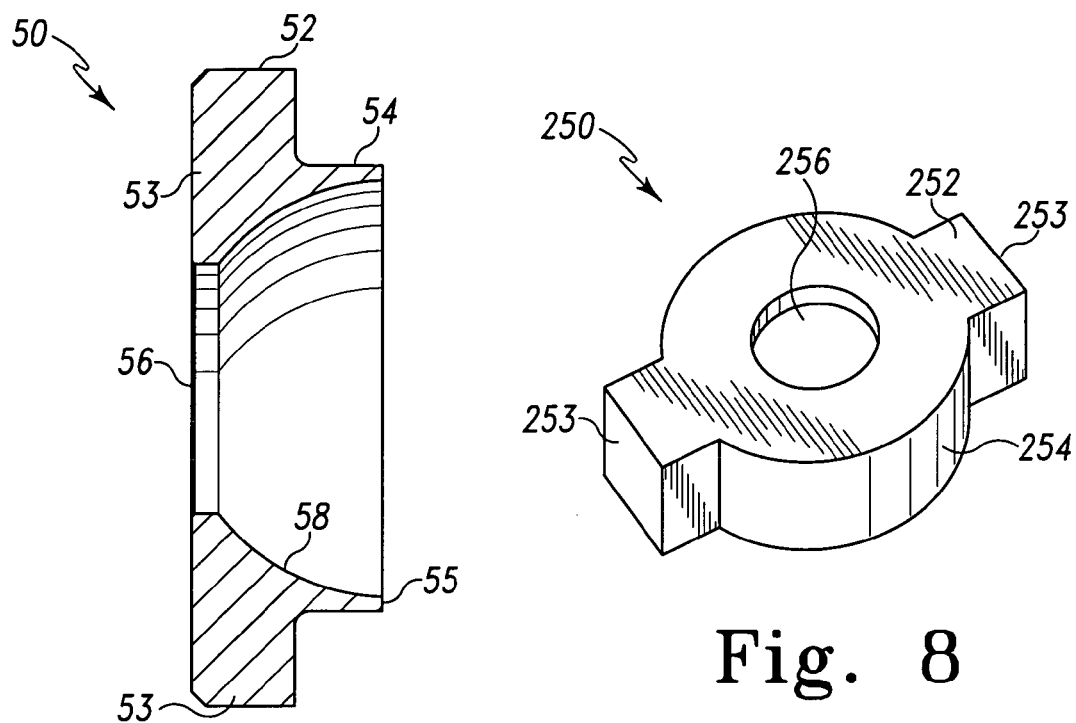
Fig. 7
Fig. 8
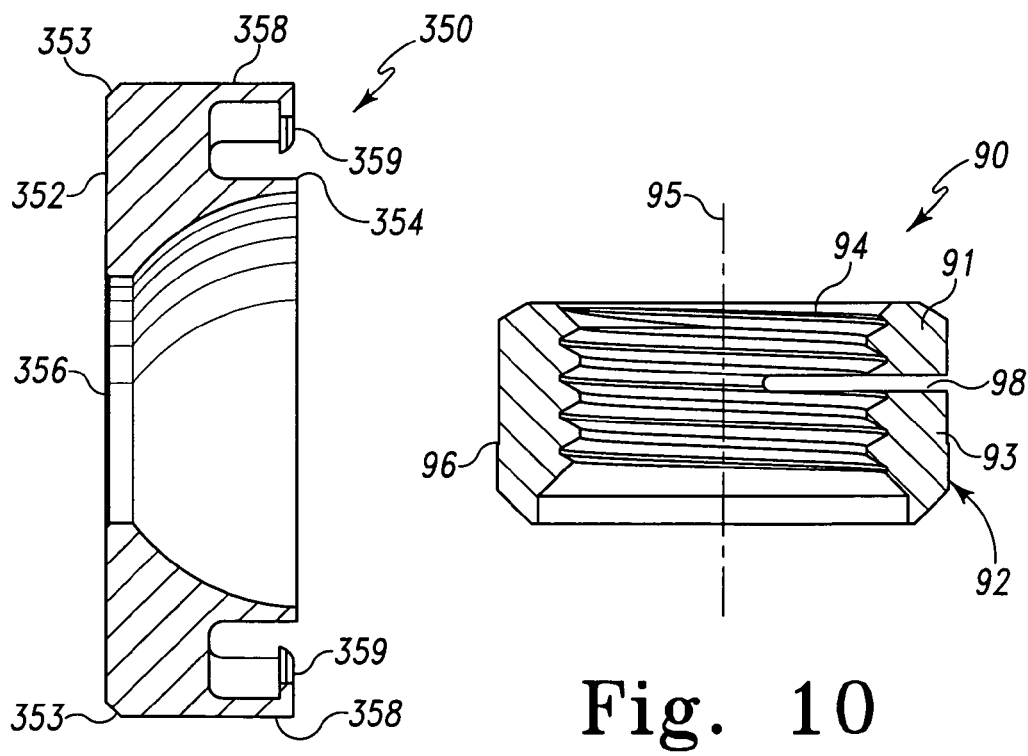
Fig. 9
Fig. 10

SPINAL IMPLANTS WITH MULTI-AXIAL ANCHOR ASSEMBLY AND METHODS

BACKGROUND

In the art of orthopedic surgery, and particularly in spinal surgery, it has long been known to affix an elongated member, such as a plate or rod, to bones in order to hold them and support them in a given position. For example, in a procedure to fuse damaged, diseased, malformed, or otherwise abnormal or injured vertebrae, the vertebrae are positioned in a corrected position by a surgeon. An elongated plate is placed adjacent to one or more vertebral bodies and bone anchors, such as screws or bolts, are employed to secure the plate to the vertebral bodies. The anchors and plate are secured to each other to minimize or prevent relative movement. In this way, the vertebral bodies may be held and/or supported in proper alignment for healing.

There remains a need for systems, devices and methods that facilitate positioning and attachment of implants to one or more vertebrae of the spinal column, that provide various attachment modes of the plate to one or more vertebrae of the spinal column, and that provide multi-axial capabilities for the anchor assemblies employed in attaching the plate to one or more vertebrae of the spinal column.

SUMMARY

The present invention relates to orthopedic implant systems and methods for use in stabilizing bone members in a desired spatial relationship in correcting bone misalignment disorders, to provide stabilization along one or more vertebral levels, or for spinal or other bone fusion. A multi-axial anchor assembly is engageable to an elongate implant member, such as a plate or rod member, to secure the plate or rod member to one or more vertebrae of the spinal column.

According to one aspect, an anchor assembly is provided that comprises an anchor member including a head and a lower portion extending from the head for engagement with a bone member. The anchor assembly further includes a coupling member pivotally coupled to the head of the anchor. The coupling member includes a lower receiver portion defining an interior receptacle for receiving said head and a post extending from the lower receiver portion away from the head. The post is configured to engage a locking member. The lower receiver portion defines at least one sidewall opening in communication with an exterior of the coupling member. The anchor assembly further includes a crown positioned in the receptacle of the coupling member about the head of the anchor member. The crown includes a seat portion in communication with the at least one sidewall opening for positioning in contact with an implant member positioned about the post of the coupling member to secure the implant member between the locking member and the seating portion.

According to another aspect, a spinal plating system comprises an elongate plate member including at least one opening extending therethrough between an upper surface and an opposite lower surface positionable along the spinal column. The system also comprises an anchor assembly engageable to the plate member. The anchor assembly includes a coupling member having a post positionable through the at least one opening and a receiver portion including a receptacle positionable adjacent the lower surface of the plate member. The anchor assembly includes an anchor member with a head pivotally captured in the receptacle of the receiver portion and a lower portion extending from the head for engaging a bony structure of the spinal column. A crown is positioned adjacent the head in the receptacle and includes a seat portion extending through the coupling member along the lower surface of the plate member. A locking member is engageable to the post and positionable in contact with the upper surface of the plate member to secure the lower surface of the plate member in contact with the seat portion of the crown.

According to a further aspect, a spinal plating system comprises an elongate plate member extending along a longitudinal axis and including at least one opening extending therethrough between an upper surface and an opposite lower surface positionable toward the spinal column. The system further includes an anchor assembly engageable to the plate member. The anchor assembly includes a coupling member with a post positionable through the at least one opening and engageable with the plate member so that the coupling member is non-pivotal relative to the plate member. The coupling member includes a receiver portion with a receptacle opening away from the plate member that is positionable along the lower surface of the plate member. The anchor assembly further includes an anchor member including a head pivotally captured in the receptacle of the receiver portion. The anchor member includes a lower portion extending from the head for engaging a bony structure of the spinal column. The anchor member is pivotal relative to the plate member and the receiver portion when the post is engaged to the plate member in the at least one opening thereof.

According to another aspect, a spinal surgical method, comprises: accessing at least one vertebra of the spinal column; engaging an anchor member of an anchor assembly to the at least one vertebra, the anchor assembly including a coupling member with a receiver portion pivotally mounted about a head of the anchor member and a post extending proximally from the receiver portion and pivotal relative to the anchor member with the receiver portion; pivoting the post and receiver portion relative to the engaged anchor member to a desired position; positioning an elongate plate member about a proximal end of the post; advancing the plate member along the post to a location adjacent the receiver portion; and engaging the plate member against a crown extending from the head of the anchor member through the coupling member.

These and other aspects will be discussed further below.

BRIEF DESCRIPTION OF THE DRAWINGS

FIG. 7 is a sectional view of a crown comprising a portion of the anchor assembly of FIG. 1.

FIG. 8 is a perspective view of another embodiment crown.

FIG. 9 is a section view of another embodiment crown.

FIG. 10 is a section view of a locking member engageable to the coupling member of the anchor assembly of FIG. 1.

DESCRIPTION OF THE ILLUSTRATED EMBODIMENTS

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

A multi-axial anchor assembly is provided to secure a plate member to one or more vertebrae of the spinal column. The anchor assembly includes an anchor member pivotally coupled in a receiver portion of the coupling member. The coupling member includes a post extending proximally from the anchor member for receiving the plate member thereabout. The anchor member is pivotal relative to the plate when the post is positioned through an opening in the plate member. In one embodiment, the coupling member can be engaged to the plate member such that the coupling member is constrained from pivoting in at least one direction relative to the plate member while the anchor member is pivotal in the coupling member.

In one form, the coupling member includes a crown in the receiver portion that extends between the anchor and the plate member positioned about the post. In one embodiment, the crown rigidly engages the anchor member in position relative to the coupling member and the plate member when the locking member is secured against the plate member. In another form, the coupling member includes at least one window and the crown includes a seat portion extending through the at least one window for contact with a lower surface of the plate member positioned about the post. The locking member firmly engages the plate member against the seat portion of the crown when the locking member is positioned against the upper surface of the plate member.

In another form, a multi-axial anchor assembly is provided that includes a coupling member for receiving a plate member thereabout and an anchor member extending distally of the coupling member. Before it is firmly engaged to the plate member with a locking member, the coupling member is received in an elongated slot of the plate such that is non-pivotal transversely to a longitudinal axis of the slot while the anchor member is pivotal in all direction relative to the coupling member. When the locking member is secured to firmly engage the plate to the coupling member, the coupling member and the anchor are fixed relative to one another and relative to the plate.

Figure 14:
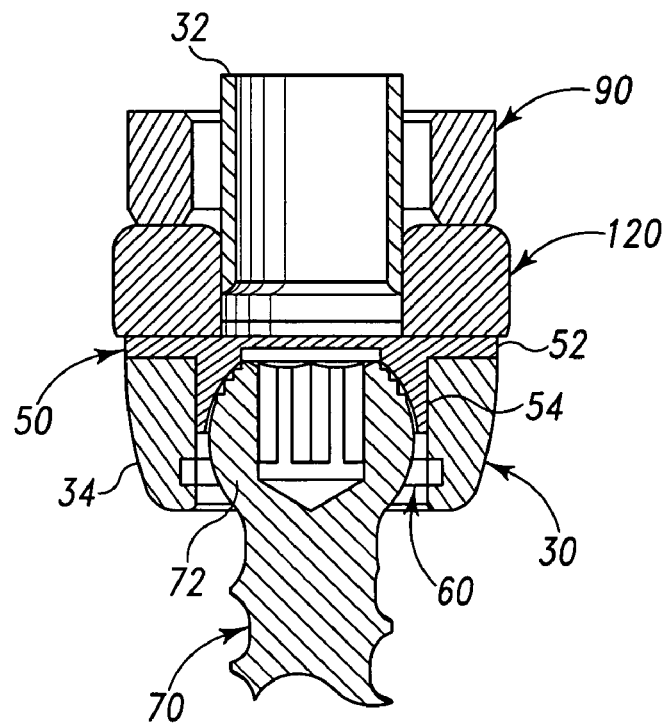
FIG. 14 is a sectional view through line 14-14 of FIG. 13.

Referring now to FIGS. 1-5 there is shown a multi-axial anchor assembly 20 having a first orientation aligned along longitudinal axis 21. Anchor assembly 20 includes a coupling member 30 and an anchor member 70 pivotally engaged to coupling member 30 with a clip 60. Anchor member 70 is pivotal about longitudinal axis 21 to a desired orientation relative thereto. A crown 50 is received in coupling member 30 adjacent anchor member 70, and includes at least seat portion that extends outwardly from coupling member 30 through windows 48. Crown 50 is positionable against a lower surface of a plate member positioned about coupling member 30, and a locking member 90 (FIG. 10) is engageable to coupling member 30 to secure the plate member against crown 50, as shown in FIG. 14. The downwardly or distally directed securing force supplied by engagement of locking member 90 can also seat crown 50 on anchor member 70 to rigidly engage anchor member 70 in the desired position relative to coupling member 30.

Figure 6:
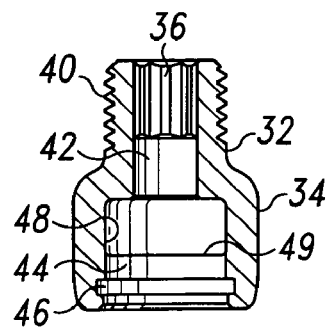
FIG. 6 is a sectional view of a coupling member comprising a portion of the anchor assembly of FIG. 1.

Further features of coupling member 30 will now be discussed with reference to FIGS. 1-6. Coupling member 30 includes a proximally extending post 32 and a lower receiver portion 34 centered about longitudinal axis 21. Post 32 includes a reduced size relative to receiver portion 34 so that post 32 can pass through an opening of the plate member while at least a portion of the receiver portion 34 is sized to prevent passage through the opening of the plate member. As shown in FIG. 6, coupling member 30 includes an upper passage portion 42 extending through post 32 in communication with a receptacle 44 defined in receiver portion 34. Receiver portion 34 includes an inner circumferential groove 46 adjacent receptacle 44 for receiving and retaining clip 60 therein.

Figure 3:
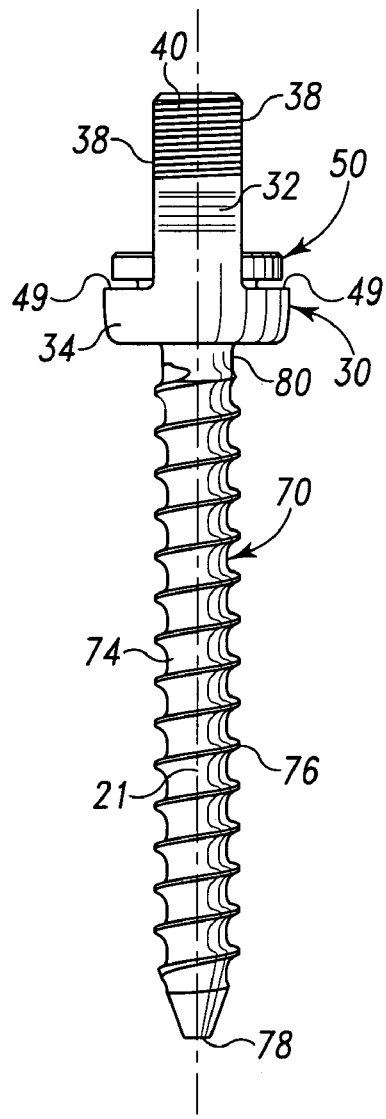
FIG. 3 is an assembled elevational view of the anchor assembly of FIG. 1.
Figure 4:
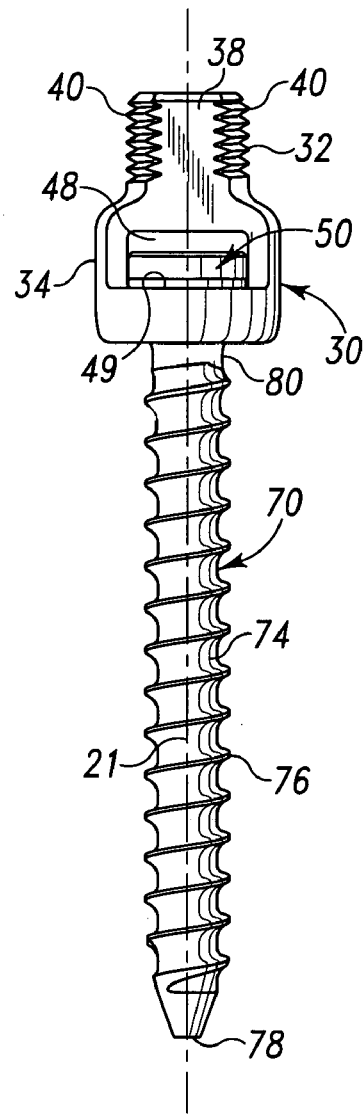
FIG. 4 is an assembled elevational view of the anchor assembly of FIG. 1 rotated 90 degrees about its longitudinal axis from its FIG. 3 orientation.
Figure 5:
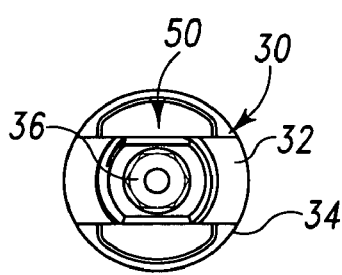
FIG. 5 is a top plan view of the anchor assembly of FIG. 4.

Receiver portion 34 further includes at least one opening so that crown 50 communicates with the exterior of coupling member 30. In the illustrated embodiment, coupling member 30 defines windows 48 in opposite sides thereof in communication with receptacle 44. As discussed further herein, at least a portion of crown 50 projects through windows 48 for contact with a plate member positioned about post 32. Crown 50 is sized to project outwardly from post 32 so that the plate member positioned thereabout will be supported by crown 50. Furthermore, as shown in FIG. 3, post 32 includes opposite flats 38 and opposite arcuate threaded portions 40 extending therebetween. As discussed below and shown in FIG. 14, flats 38 engage the sides of an elongated slot or other opening in the plate member. In one embodiment, post 32 prevents the plate member from twisting or rotating about post 32 by engaging the sides of an elongate slot of the plate. Threaded portions 40 threadingly engaging a locking member 90 positioned about post 32.

Upper passage portion 42 of post 32 defines a proximally opening tool engaging portion passage 36 with an internal surface configured to engage a tool to facilitate rotating coupling member 30 about longitudinal axis 21. In addition, passage portion 42 can be sized to permit passage of a driving instrument to engage the anchor member captured in receiver portion 34 and apply a driving force directly to the anchor member through coupling member 30.

Figure 1:
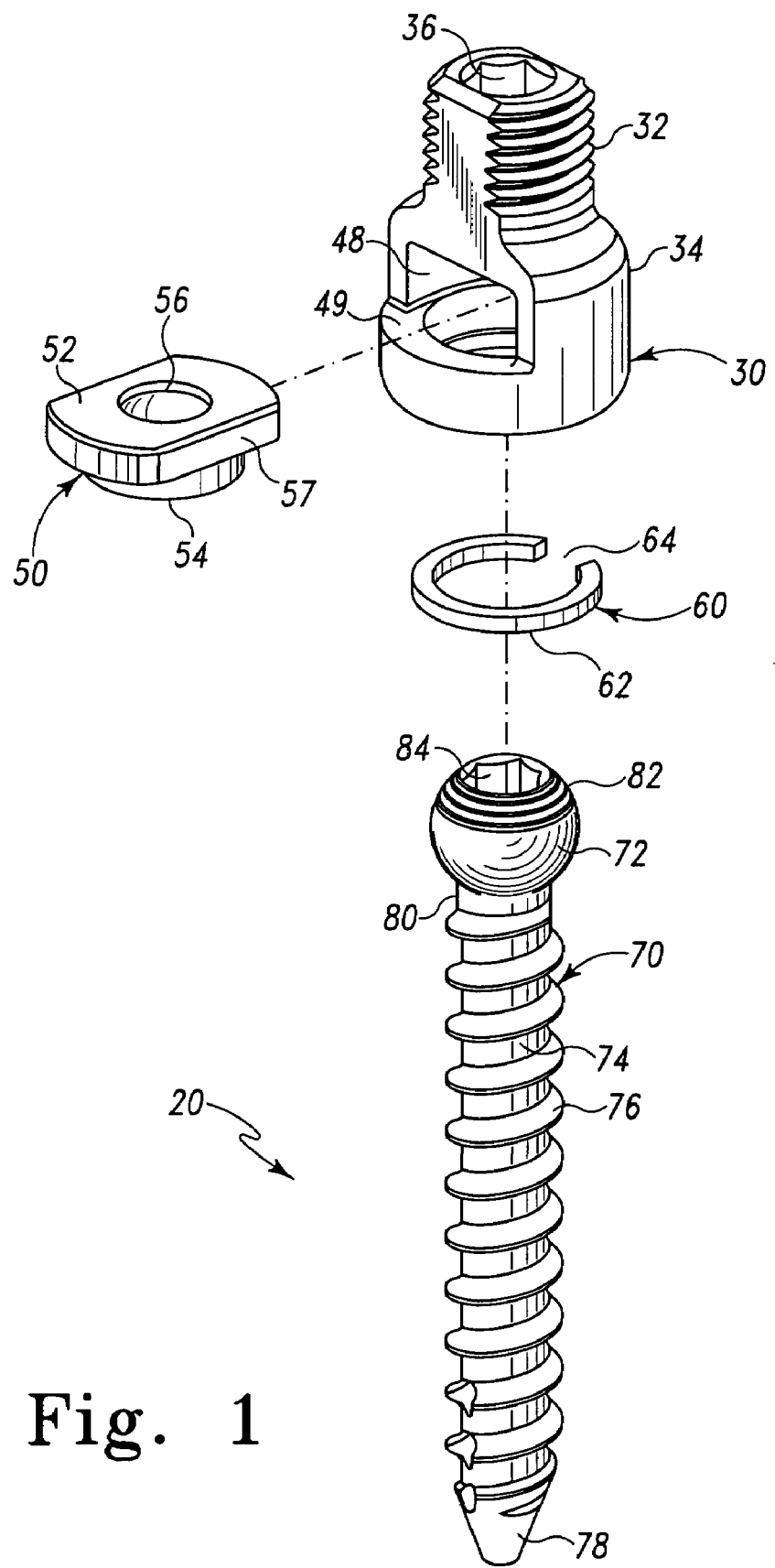
FIG. 1 is an exploded perspective view of a multi-axial anchor assembly.
Figure 2:
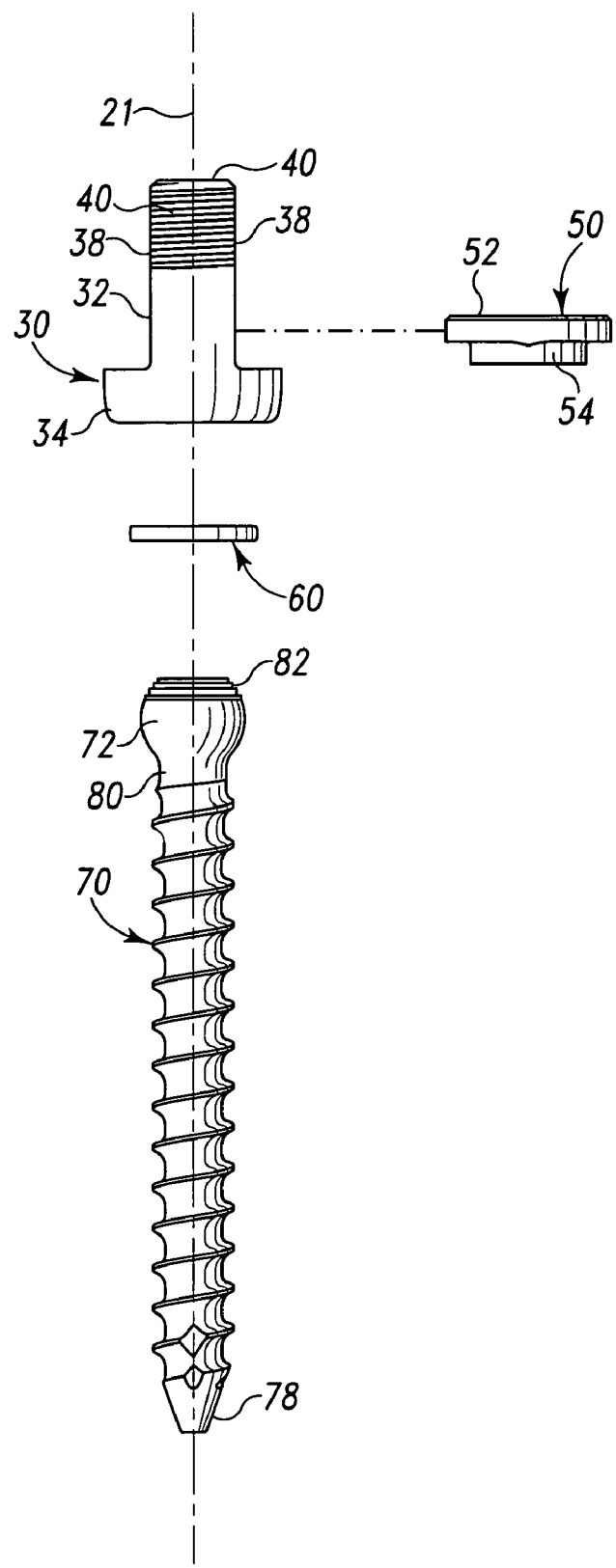
FIG. 2 is an exploded elevational view of the anchor assembly of FIG. 1.

Referring now to FIG. 7, a sectional view of crown 50 is shown. Crown 50 includes a seat portion 52 having arms 53 extending from a lower cup portion 54. As shown in FIG. 1, seat portion 52 forms an oval shape with linear wall portions 57 extending between arms 53. Cup portion 54 includes a semi-spherical shape projecting from seat portion 52 with an opening formed at its lower or distal end 55. Cup portion 54 defines a receptacle 58 having a concavely curved inner surface adapted to receive the shape of the head of anchor member 70 positioned in coupling member 30. A through-hole 56 extends through seat portion 52 and is in communication with the receptacle 58 in cup portion 54, allowing placement of a driving instrument therethrough for engagement with a tool recess in the head of the anchor member 70 positioned in receptacle 58.

FIG. 8 shows another embodiment crown 250 having an upper or proximal seat portion 252 and a lower or distal cup portion 254. Cup portion 254 defines a receptacle which extends from seat portion 252 and opens distally opposite seat portion 252. The head of the anchor member 70 is received in the receptacle defined by cup portion 254. At least a portion of seat portion 252 is formed by a pair of outwardly projecting arms 253 extending proximally and distally along cup portion 254. A through-hole 256 extends through seat portion 252 and is in communication with the receptacle defined by cup portion 254.

FIG. 9 shows another embodiment crown 350, which is similar to crown 50. Crown 350 includes an upper or proximal seat portion 352, a lower or distal cup portion 354 and a through-hole 356. Arms 353 extend outwardly from cup portion 354, and include flange members 358 extending distally therefrom at the outer ends of respective ones of the arms 353. The distal end of each flange member 358 includes inwardly facing lip 359. In use, lips 359 are supported on window ledges 49 of coupling member 30 with the anchor member 70 pivotally captured in receiver portion 34. Flange members 358 and lips 359 maintain clearance between the head of the anchor member 70 positioned adjacent crown 350 so that when the plate member is secured against seat portion 352, flange members 358 and lips 359 maintain clearance between the head of the anchor member 70 and crown 350 so that the anchor member 70 can pivot in coupling member 30. Crown 350 may be employed in situations where dynamic stabilization of one or more vertebrae is desired. Dynamic stabilization can also be provided by any one or combination of removing the ridges 82 from the head 72 of the anchor member 70 (FIG. 11), providing a resilient crown member, or maintaining separation between the crown member and the head of the anchor member.

FIG. 10 shows one embodiment of a locking member 90 engageable to post 32 of coupling member 30. Locking member 90 includes a body 92 having a sidewall 96 extending about a threaded through-bore 94. Through-bore 94 extends along a longitudinal axis 95 that is alignable along the longitudinal axis 21 of anchor assembly 20. A slot 98 extends through sidewall 96 and is communication with through-bore 94, separating locking member 90 into proximal and distal portions 91, 93. When locking member 90 is engaged about post 32 and the distal portion is in contact with the plate member 120, as shown in FIG. 14, further tightening of locking member 90 against the plate member causes the proximal portion 91 to deflect toward the distal portion 93. This provides an interference fit or cross-threading between threads of post 32 and the threads of locking member 90, preventing locking member 90 from loosening in situ. Other embodiments contemplate other forms for locking members 90, including a locking member without slot 98, a locking member with break-off portions to ensure proper torque is applied during engagement, or a locking member providing other engagement relationships with post 32, such as a bayonet-lock, interference fit, or fused connection.

Figure 11:
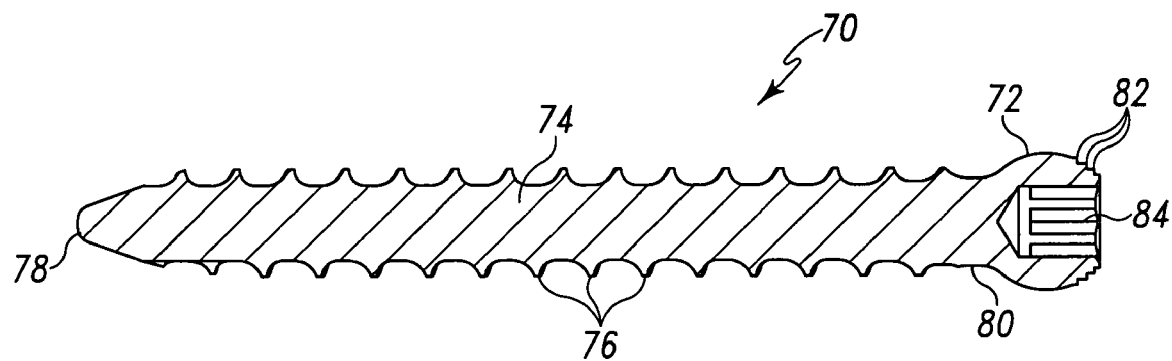
FIG. 11 is a section view of a first embodiment anchor member of the anchor assembly of FIG. 1.

FIG. 11 shows one embodiment of anchor 70. Anchor 70 includes enlarged head 72 at a proximal end thereof, and a distal portion that includes a threaded shaft 74 extending distally from head 72 to a tapered distal tip 78. Shaft 74 includes a thread profile 76 extending therealong configured to engage bony tissue. Shaft 74 and thread profile 76 may include any suitable form, including flutes along all or a portion of shaft 74, and uniform or varying thread pitches, thread heights, thread widths, and shapes along shaft 74. Thread profile 76 can be configured for insertion into a drilled and tapped hole, can be configured as a self-tapping thread, or can be configured as a self-drilling and self-tapping thread. A non-threaded neck 80 is provided between head 72 and shaft 74, although threads may extend along and/or run-out along neck 80. Head 72 further includes a tool engaging recess 84 opening at the proximal end thereof that can include any suitable configuration for receiving a driving tool to apply a rotational driving force to anchor member 70 and threadingly engage it to bony tissue.

Head 72 includes plurality of ridges 82 extending circumferentially therearound adjacent the proximal end thereof, although a head 72 without ridges 82 is also contemplated as discussed above. For example, dynamic stabilization of the spinal column segment can be provided with an anchor member having a smooth head that is allowed to rotate in crown 50 when the anchor assembly is engaged to the plate member with locking member 90. Ridges 82, as discussed further herein, engage or bite into crown 50 to lock anchor member 70 in position relative to coupling member 30 when engaged to a plate member with locking member 90. Ridges 82 can be formed by a series of flattened surfaces machined into head 72. Other embodiments contemplate ridges 82 formed by spikes, knurlings, teeth, or other surface features. An anchor assembly 20 having an anchor member with ridges 82 provides a rigid or static connection between the plate member and the spinal column segment.

For any plate member, it can be entirely statically engaged to the spinal column with anchor assemblies 20 having anchor members that are rigidly engaged with the respective coupling member secured to the plate member. Any plate member can be entirely dynamically engaged to the spinal column with anchor assemblies 20 having anchor members that are pivotal in the respective coupling members secured to the plate member. Combinations of rigid and dynamic anchor assemblies 20 can be employed to engage a plate member to the spinal column.

Figure 12:
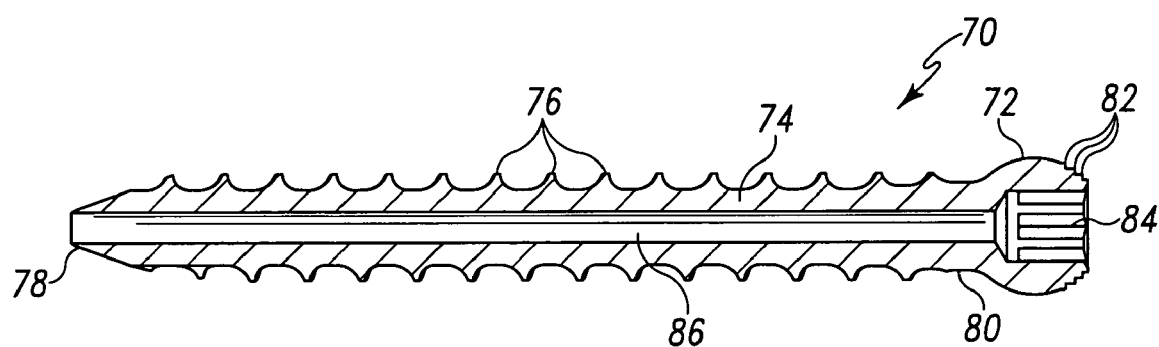
FIG. 12 is a sectional view of another embodiment anchor member of the anchor assembly of FIG. 1.

Referring to FIG. 12, there is shown another embodiment of anchor 70 in which shaft 74 is provided with a lumen 86 extending longitudinally therealong and opening at distal tip 78 and into tool engaging recess 84. Lumen 86 can be configured to receive a guidewire or other guiding member to guide placement of anchor 70 to the desired location relative to the bony structure. Lumen 86 can also be employed to deliver bone graft or other bone growth promoting and/or therapeutic material into the bony structure in which anchor member 70 is engaged. Still other embodiments contemplate shaft 74 including one or more fenestrations or openings in communication with lumen 86 that are located between neck 80 and distal tip 78.

Still other embodiment contemplate that anchor member 70 includes a distal portion with other configurations for engaging bony tissue. For example, the distal portion may include a cable, a hook, a clamp, a staple, a smooth shaft with wings or gulls, an expandable anchor, a body for positioning in a disc space between vertebrae, or other structure for engaging bony structure.

Figure 13:
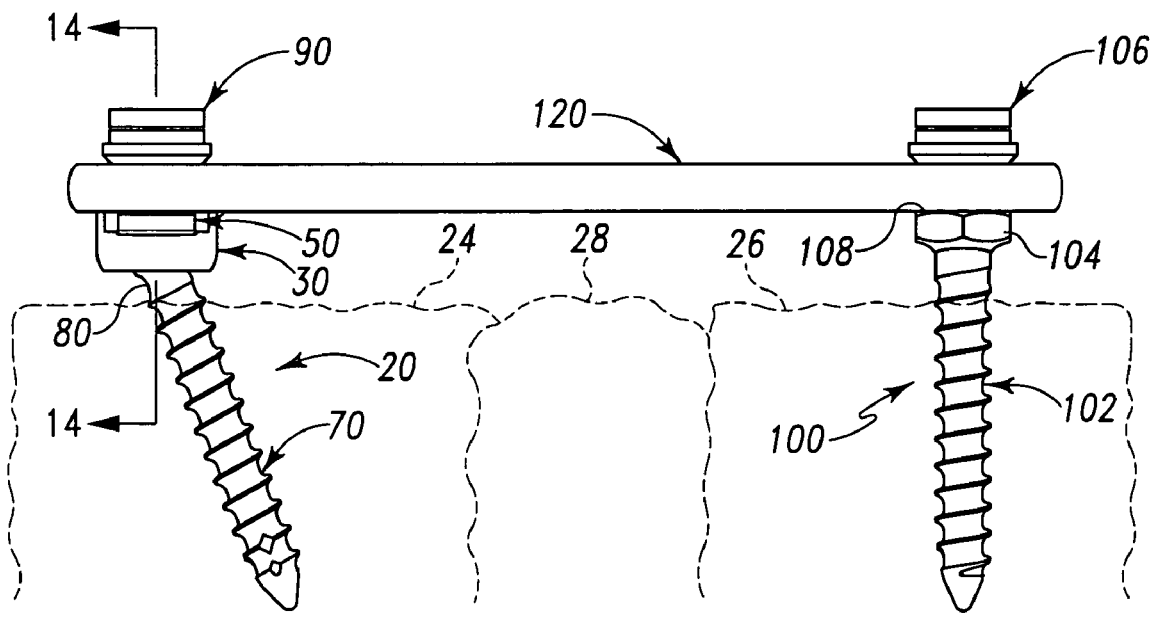
FIG. 13 is an elevational view of a plate member secured to the multi-axial anchor assembly of FIG. 1 with the locking member of FIG. 8, and also with an uni-axial anchor secure to the plate member.

Referring now to FIG. 13, there is shown an elongate plate member 120 engaged to vertebrae 24, 26 on opposite sides of disc space 28 with a multi-axial anchor assembly 20 and an uni-axial anchor 100. It should be understood that plate member 120 can be engaged to the vertebrae with any combination of multi-axial and/or uni-axial anchor assemblies. Uni-axial anchor assembly 100 includes a threaded shaft member 102 and a proximal head member 104 extending therefrom that is integrally formed therewith. Proximal head member 104 extends through plate member 120, and includes a lower support member 108 against which the lower surface of plate member 120 is positioned. A locking member 106 is engaged to head member 104 and clamps or seats plate member 120 against lower support member 108.

The connection of plate member 120 with multi-axial anchor assembly 20 is also shown in section view in FIG. 14. Plate member 120 is positioned so that its lower surface is in contact at least partially with seat portion 152 of crown 150. Post 32 of coupling member 130 extends through plate member 120, and locking member 90 is positioned about post 32. As locking member is advanced along post 32 toward the upper surface of plate member 120, locking member 90 exerts a force against plate member 120 and firmly secures it between seat portion 52 of crown 50 and locking member 90. In the illustrated embodiment, the securing force pushes crown 50 downwardly against head 72 of anchor 70. For embodiments contemplating rigid fixation, the anchor member 70 includes ridges 82 that bite into crown 50 to lock anchor member 70 in position relative to coupling member 30 and plate member 120.

Figure 17:
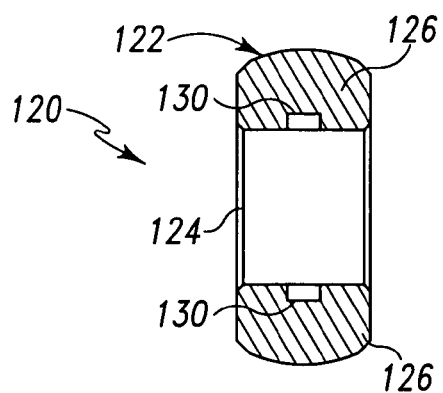
FIG. 17 is a sectional view through line 17-17 of FIG. 16.
Figure 15:
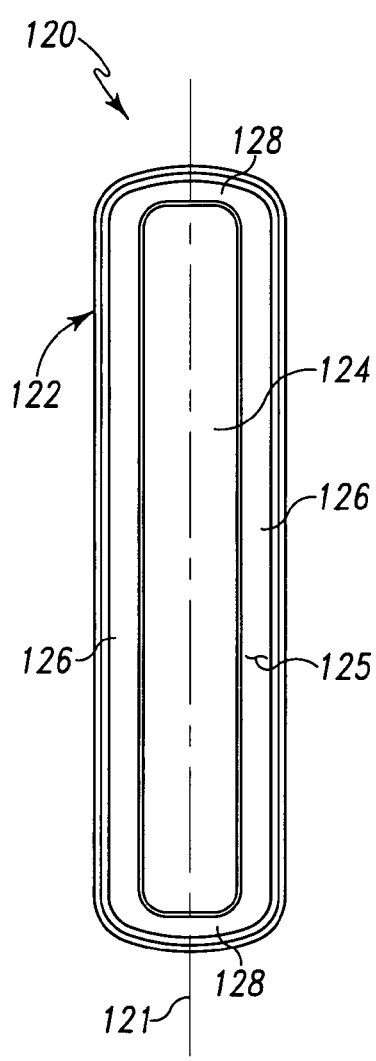
FIG. 15 is a plan view of one embodiment plate member.
Figure 16:
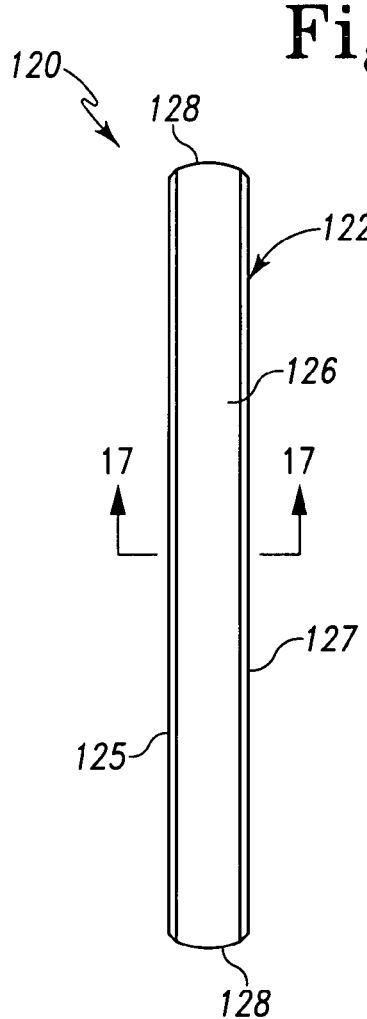
FIG. 16 is an elevational view of the plate member of FIG. 15.

Referring now to FIGS. 15-17, further details of one embodiment of plate member 120 are shown. Plate member 120 includes an elongate body 122 extending along a longitudinal axis 121. Body 122 includes at least one opening in the form of an elongate slot 124 centered and extending along longitudinal axis 121. Slot 124 opens at upper and lower surfaces 125, 127. Side rails 126 extend longitudinally along opposite sides of slot 124, and end rails 128 extend between side rails 126 at the ends of body 122.

Side rails 126 include an inner surface 129 extending along slot 124 and an outer surface 131. As shown in FIG. 17, body 122 includes longitudinal grooves 130 in inner surface 129 extending along slot 124. The plate surfaces and edges of rails 126, 128 transitioning between the upper and lower plate surfaces and between the inner and outer rails surfaces can be rounded or chamfered to eliminate any sharp edges or abrupt transitions between plate surfaces.

Figure 18:
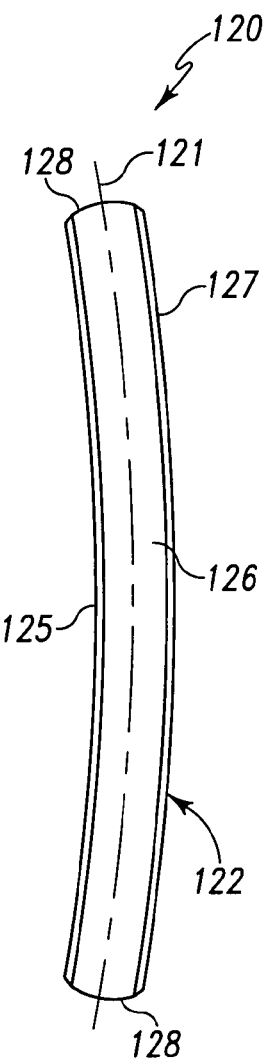
FIG. 18 is an elevational view of the plate member of FIG. 15 with a curved longitudinal profile.

In FIG. 18, there is shown plate member 120 with a curved profile along its longitudinal axis 121. Upper surface 125 is concavely curved, and lower surface 127 is convexly curved. The curved configuration can be provided by pre-bent plates, or by the surgeon bending the plate during surgery to provide the desire fit with the patient's anatomy.

Figure 19:
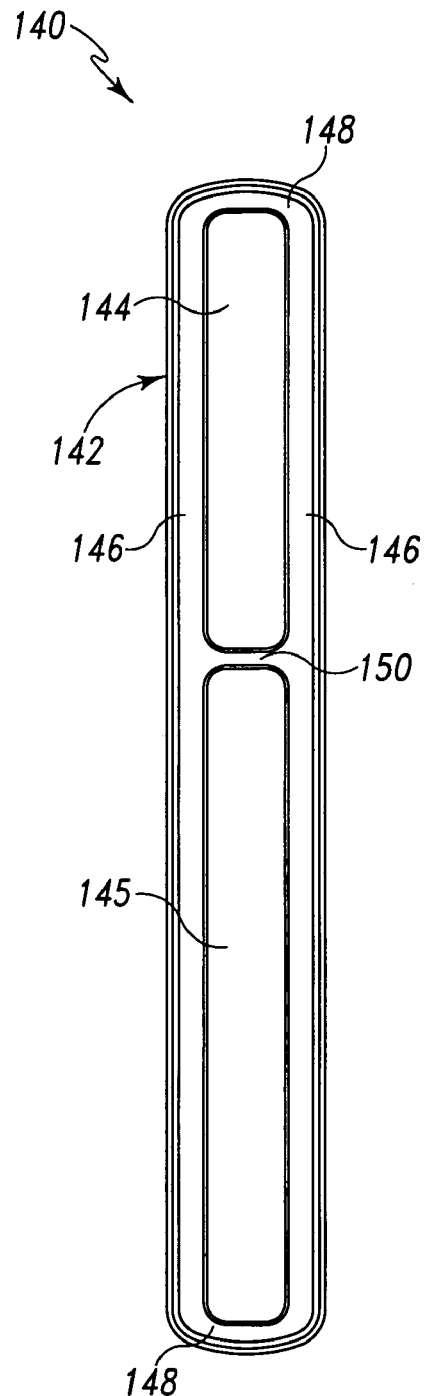
FIG. 19 is a plan view of another embodiment plate member.

In FIG. 19, there is shown another embodiment plate member 140. Plate member 140 is similar to plate member 120, and includes an elongated body 142 having opposite side rails 146 and opposite end rails 148. Plate member 140 includes openings in the form of a pair of elongated slots 144, 145 are formed along body 142, and intermediate rail 150 is located between slots 144, 145 and extends between side rails 146. In the illustrated embodiment, slot 144 is shorter than slot 145. Other embodiments contemplate slots of equal length, and plate members with more than two slots. For any of the plate member embodiments, the slots may include scallops, recesses or other features to facilitate placement or engagement of anchors therewith. It is also contemplated that the plate members may include two or more slots adjacent to and extending along one another. Still other embodiments contemplate the plates are provided with openings between the upper and lower surfaces in the form of circular holes.

Figure 20:
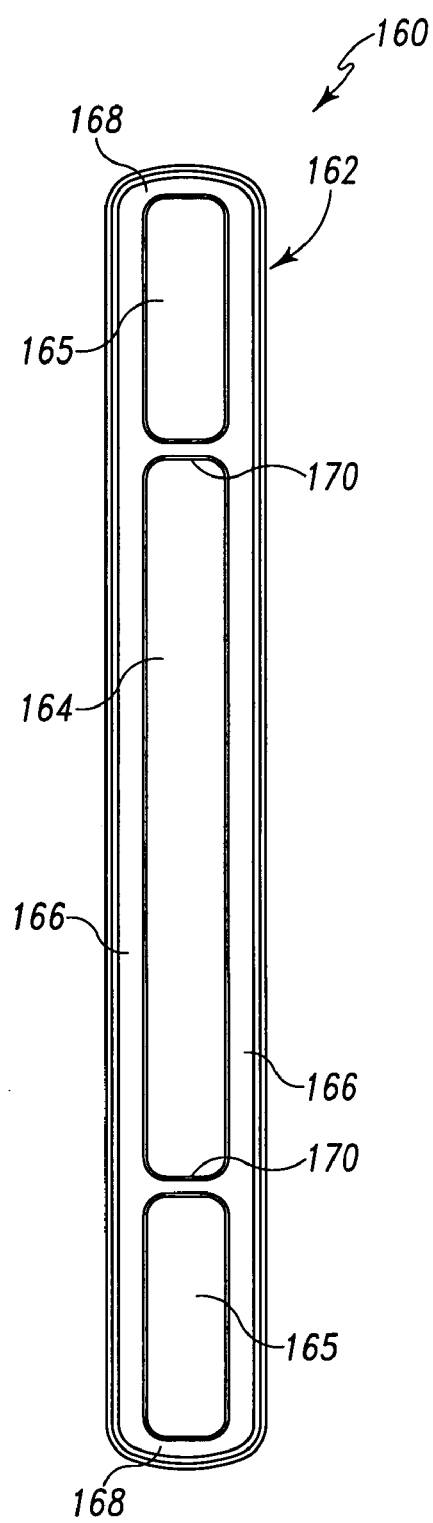
FIG. 20 is a plan view of another embodiment plate member.

In FIG. 20 there is shown another embodiment plate member 160. Plate member 160 include a body member 162 having side rails 166 and end rails 168. A pair of end slots 165 are provided adjacent end rails 168, and an intermediate slot 164 is provided between end slots 165 with intermediate rails 170 located between intermediate slot 164 and respective ones of the end slots 165. In the illustrated embodiment, intermediate slot 164 is longer than end slots 165.

Figure 21:
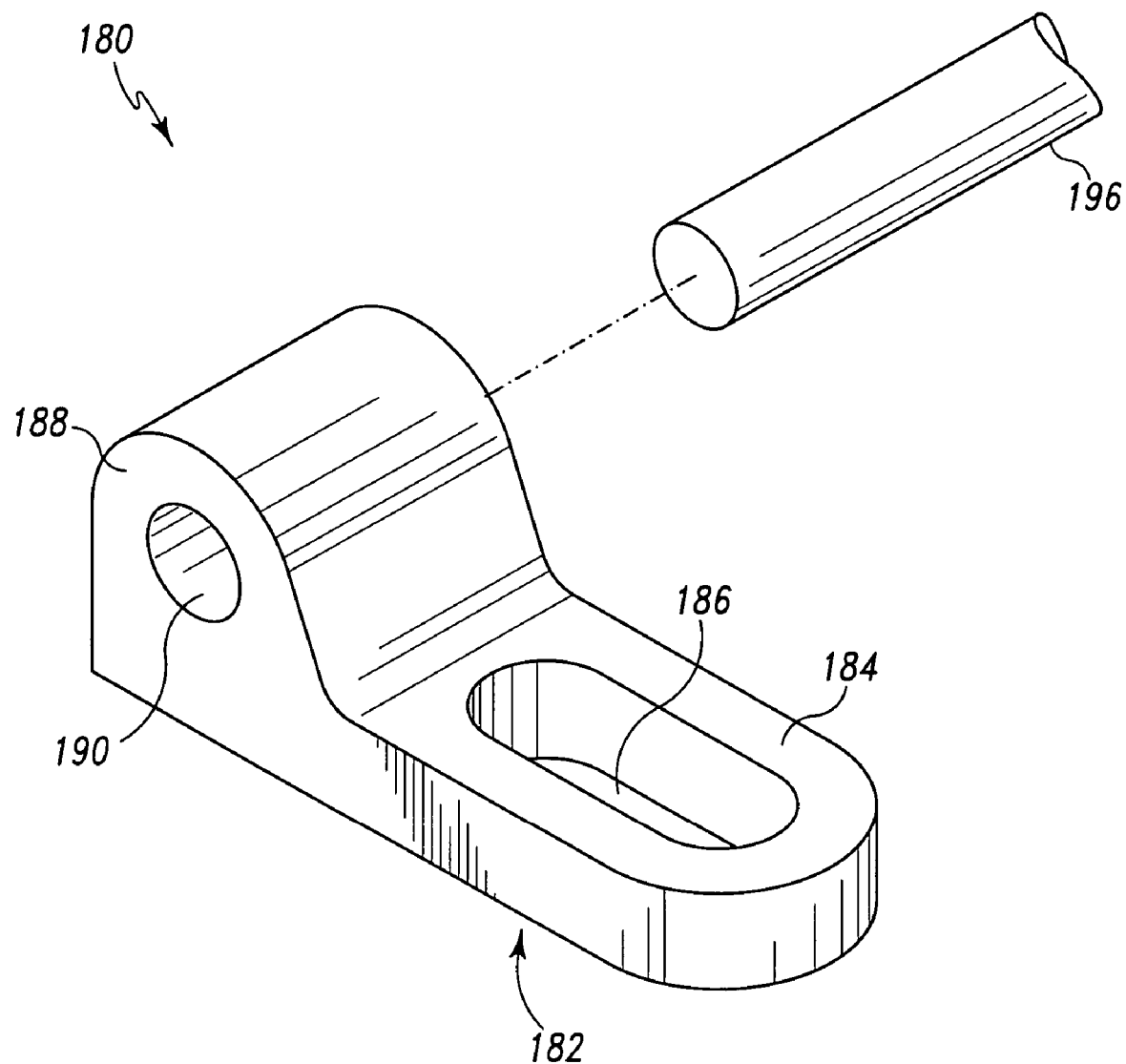
FIG. 21 is a perspective view of another embodiment plate member with a rod receiving portion.

In FIG. 21 there is shown another embodiment plate member 180. Plate member 180 includes a body 182 having an anchor assembly engaging portion 184 and a rod receiving portion 188. Anchor assembly engaging portion 184 includes an opening therethrough in the form of an elongate slot 186 for receiving an anchor assembly, such as anchor assembly 20. Slot 186 allows the positioning of the plate member 180 to be adjusted by securing it thereto with anchor assembly 20. Rod receiving portion 188 defines a passage 190 for receiving an elongate spinal rod 196 therein. Passage 190 extends transversely to slot 186. In the illustrated embodiment, rod receiving portion 188 is a cylindrical member that completely surrounds passage 190. However, other embodiments contemplate a passage that is open along all or a portion of a side thereof, a rod receiving portion 188 comprising multiple components for clamping or gripping the rod in passage 190, and other suitable arrangements for receiving and/or engaging a rod or other elongate implant member.

Figure 22A:
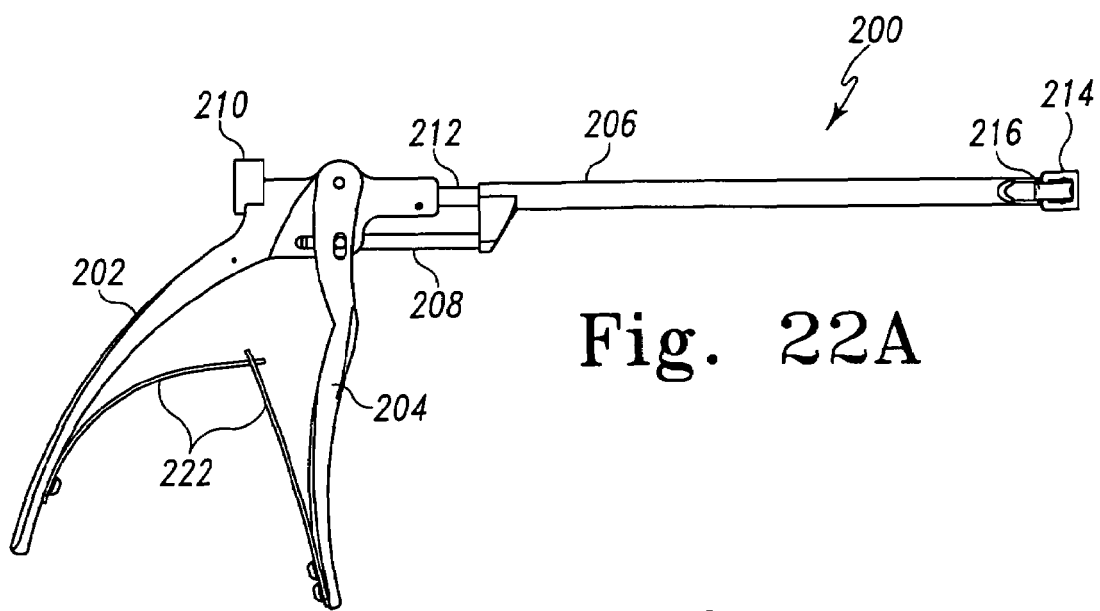
FIG. 22A is an elevation view of an instrument for holding a plate member.
Figure 22B:
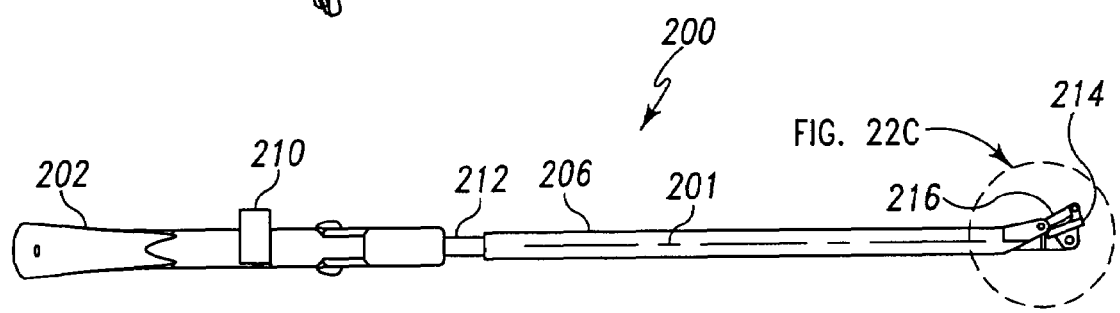
FIG. 22B is a top view of the instrument of FIG. 22A.
Figure 22C:
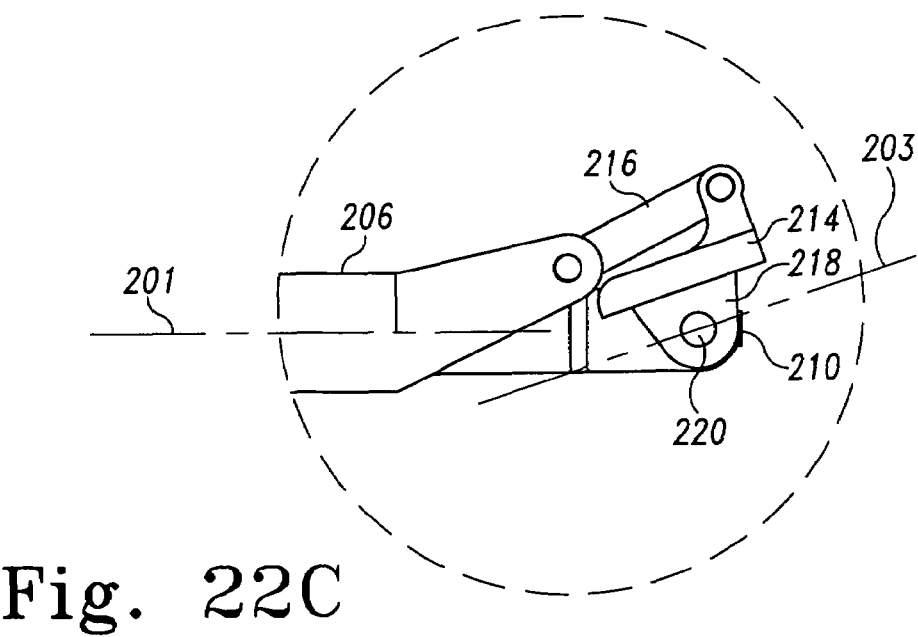
FIG. 22C is an enlarged view of a distal holding portion of the instrument of FIG. 22A in a first orientation.

FIGS. 22A-22E show one embodiment plate holder 200 engageable in, for example, grooves 130 to hold the plate member for delivery to the operative site. Examples of holding instruments are provided in U.S. patent application Ser. No. 10/202,918 filed on Jul. 25, 2002, which is incorporated herein by reference in its entirety. Plate holder 200 includes a handle member 202 and a lever member 204 pivotally coupled thereto. A shaft member 206 is coupled to lever member 204 with a first link 208. A mounting shaft 212 extends through shaft member 206 from handle member 202, and includes a locking member 210 having a proximal knob portion and a shaft extending through mounting shaft 212, as shown in FIG. 22C.

The distal end of mounting shaft 212 includes a mounting member 214 pivotally mounted thereto. Mounting member 214 includes an engaging portion 218 sized to fit within, for example, slot 124 of plate member 120. Engaging portion 218 can also be sized to fit within an opening or slot of any plate member embodiment discussed herein. In the illustrated embodiments, engaging portion 218 includes engaging members 220 to engage groove 130 of plate member 120. Engaging members 220 can be in the form of ball members or stems that can recess into engaging portion 218 for positioning in slot 124, and can then be moved outwardly to engage groove 130 and mount plate member 120 to mounting member 214. Locking member 210 can then be rotated within mounting shaft 212 by its proximal knob so that its distal end portion in engaging portion 218 secures engaging members 220 in engagement with the plate member.

Figure 22D:
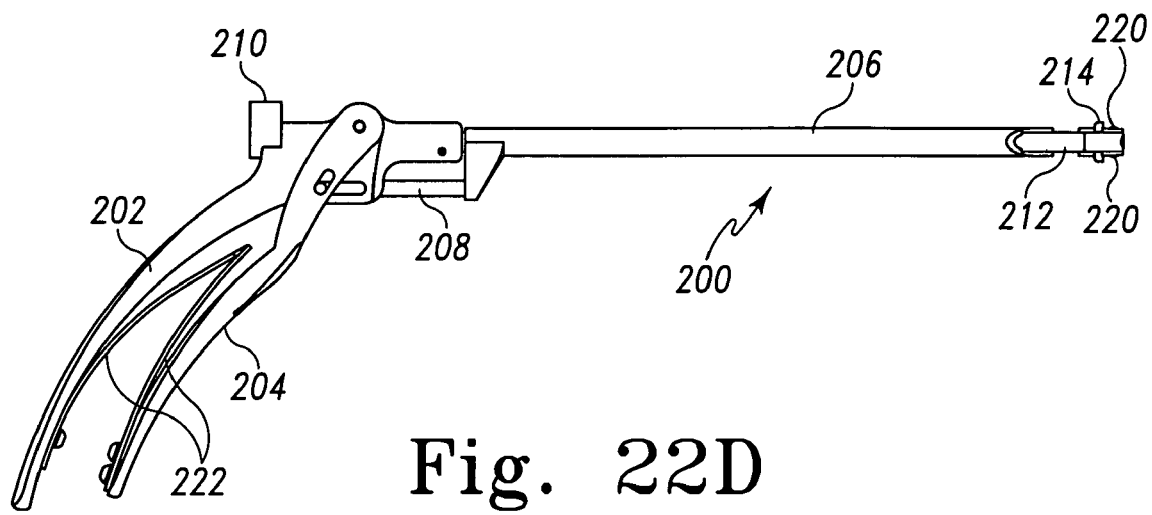
FIG. 22D is an elevation view of the instrument of FIG. 22A with the holding portion in a second orientation.
Figure 22E:
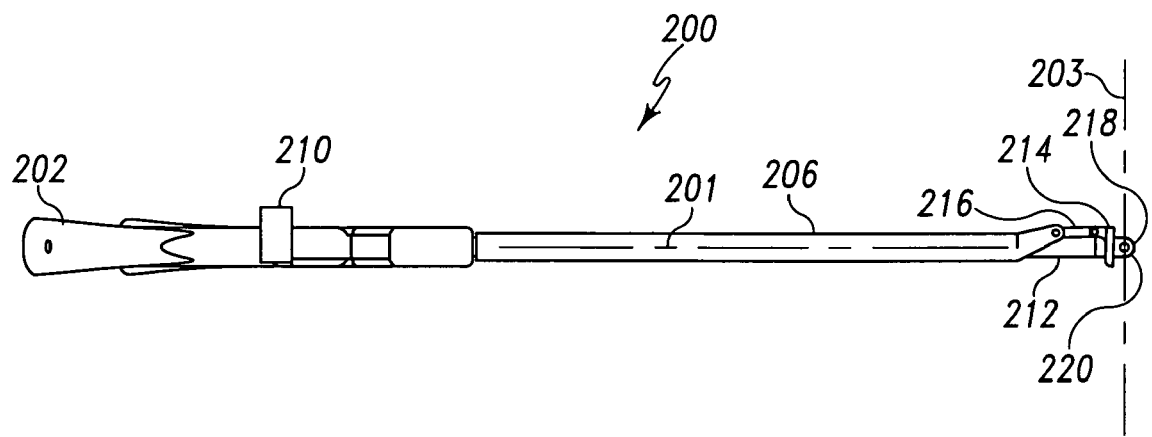
FIG. 22E is a top view of the instrument of FIG. 22A with the holding portion in the second orientation.

Shaft member 206 is movable relative to handle member 202 and mounting shaft 212 by moving lever 204 between an open position as shown in FIG. 22A and a closed position as shown in FIG. 22D. Spring mechanism 222 normally biases lever member 204 and handle member 202 to the open position. In the open position, mounting member 214 is oriented so that the plate member extends along an axis 203 (FIG. 22C) which is oriented more along the longitudinal axis 201 of instrument 200. In the closed position, link 216 extending between shaft member 206 and mounting member 214 pivots mounting member 214 about the distal end of mounting shaft 212 as shaft member 206 is moved proximally with lever 204. In the closed position, axis 203 and thus the plate member secured to mounting member 214 extend perpendicular to or substantially transversely to the longitudinal axis 201 of instrument 200. Thus, instrument 200 facilitates placement of the plate through narrow incisions or tubes by holding the plate in a first orientation that is oriented along the approach to the spinal column and thereafter allowing the plate to be remotely pivoted into alignment along the spinal column.

Instrument 200 is just one example of a suitable instrument for holding and delivering plate members to the spinal column for engagement thereto with the anchor assemblies discussed herein. Other examples of holding instruments include forceps or other grasping instruments, instruments with fasteners to engage the plate, and instruments that provide an interference fit with the plate. The instruments can engage in the plate slots or holes, clamp between the outer surfaces of the plate, or hold the plate between a slot or hole surface and an outer surface of the plate, for example. Still other examples contemplate the plate is manually grasped and delivered to the surgical site.

In one embodiment, the plate member is sized to contact neighboring vertebrae, and includes at least one opening adjacent those vertebrae so that the coupling member of the anchor assembly can be placed through the at least one opening when the anchor member of the anchor assembly is engaged to the underlying bony structure. In another embodiment, the anchor assemblies can be provisionally captured on the plate member with locking member 90 prior to engagement with the bony structure. The plate members may also be sized and configured to extend across more than two vertebrae for multi-level stabilization procedures, or configured for engagement with a single vertebrae with a receiving member for receiving an elongate connecting element, such as a rod or plate, positionable along two or more vertebrae.

The plate members can be pre-bent or bent during surgery to include a curvature, for example, to replicate or conform to a natural or desired spinal curvature. It will be understood that any curvature appropriate for one or more segments of the spine (whether cervical, thoracic, lumbar or sacral) could be incorporated into plate member. Such curvatures can include entirely convex, entirely concave, entirely straight (i.e. essentially planar), and combinations thereof. It is further contemplated that the plate can be engaged to the anterior, oblique, lateral, or posterior bony portions of one or more vertebrae.

The illustrated embodiments of the plate members herein do not show a retaining member on or engageable to the plate member to prevent or resist backout of the locking member. However, the plate members may also be provided with one or more retaining elements to prevent backout of any portion of the anchor assembly relative to the plate member. The retaining elements may be any one or combination of a set screw, set screw and washer, spring-loaded member, sliding washer or other similar device attached to, captured on or integrally formed with the plate member.

For ease of use, a kit containing one or more of the parts of the implant assembly may be provided. For example, a kit may include several embodiments of plate members in several different lengths, sizes, slot configurations, and/or curvatures. Lengths or sizes appropriate for cervical, thoracic, lumbar and/or sacral implantation may be included. One or more sets of multi-axial and unity-axial anchor assemblies can be provided with various anchor member sizes and coupling members adapted for attachment to one or more of the cervical, thoracic, lumbar and sacral regions of the spine may also be provided in such a kit. The kit may further include multiple multi-axial anchor assemblies that include those configured to provide rigid stabilization and dynamic stabilization of the spinal column when engaged to the plate member.

A method of using the multi-axial anchor assembly will now be described. The anchor assemblies can be employed in open surgical procedures where skin and tissue is retracted, and in minimally invasive surgical procedures where the anchor assembly and/or plate members are positioned in the patient with one or more minimally invasive access approaches formed by micro-incisions, retractors, sleeves, or expanding sleeves.

In one procedure, a surgeon will make an incision into the patient at a place relatively proximate to the vertebrae or other bone(s) to which the implant is to be attached. After the appropriate access to the surgical site is obtained, a portion of the inferior vertebra to be instrumented (e.g. the pedicle) is prepared in a standard manner. For example, an awl or drill may be used to prepare a hole, which is then probed for depth and tapped if appropriate for the anchor member. One of the anchor members is then inserted into the hole in the inferior vertebra with a coupling member engaged thereto. Access to a portion of the superior vertebra (e.g. the pedicle) to be instrumented is then obtained, either via the previous incision or via a separate incision. The point on the superior vertebra at which the implant is to be attached is identified, and the vertebra is prepared as described above. Another anchor assembly is engaged to the superior vertebra, and at least one of the anchor assemblies is a multi-axial anchor assembly. The process is repeated for any vertebrae between the superior and inferior vertebrae if desired.

A plate member is then inserted directly through the incision or through an access tube or retractor to the anchor assemblies. The post of each of the at least one multi-axial anchor assembly coupling members is positioned through or bottom-loaded through an opening of the plate member. The orientation and axial location of the coupling member relative to the anchor member and the plate member can be adjusted. When the plate member and anchor assemblies are in the desired position relative to one another and the spinal column, locking member 90 can be advanced to secure the respective anchor assembly and plate member relative to one another in the desired position. Prior to finally securing the plate member to the anchor assemblies, the vertebra can be compressed or distracted and maintained in this position with the secured plate member. It is further contemplated that one or more disc spaces or posterior elements between vertebrae can be fused with any one or combination of bone graft, bone material, and implants.

It will further be appreciated that the embodiments described above should be made of materials suitable for implantation within the human or other body, and may consist of inert metals like titanium or stainless steel. Other sturdy materials such as certain ceramics or plastics may also be considered. Bio-resorbable materials, such as polylactic acid compounds, may be used along with or as a part of the parts described above. In one embodiment, a non-metal plate is employed with the anchor assemblies. The engagement of the anchor assemblies to the non-rigid plate includes at least some flexibility for flexible spinal stabilization, allowing at least limited motion of the instrumented vertebral level. Spinal motion can be enhanced by providing anchor assembly 20 in a form that dynamically engages the plate member to the spinal column, as discussed above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A spinal plating system, comprising:
   an elongate plate member including at least one opening extending therethrough between an upper surface and an opposite lower surface, said lower surface being positionable along the spinal column;
   an anchor assembly engageable to said plate member, said anchor assembly including:
   a coupling member having a post positionable through said at least one opening and a receiver portion positionable adjacent said lower surface of said plate member, said receiver portion including a receptacle, wherein said coupling member further includes opposite windows;
   an anchor member including a head pivotally captured in said receptacle of said receiver portion and a lower portion extending from said head for engaging a bony structure of the spinal column;
   a crown positioned adjacent said head in said receptacle, said crown including a seat portion with opposite arms projecting through respective ones of said opposite windows along said lower surface of said plate member; and
   a locking member engageable to said post and positionable in contact with said upper surface of said plate member to secure said lower surface of said plate member in contact with said seat portion of said crown and to secured said crown in contact with said head of said anchor in said receiver portion.

2. The system of claim 1, wherein said lower portion of said anchor member includes a threaded shaft.

3. The system of claim 2, wherein said anchor member includes an unthreaded neck portion between said head and said threaded shaft.

4. The system of claim 3, further comprising a clip positioned about said neck portion and extending between said coupling member and said head, said clip being sized to prevent passage of said head therethrough to retain said anchor member in said receptacle of said coupling member.

5. The system of claim 1, wherein said head includes a plurality of ridges extending thereabout adjacent said crown.

6. The system of claim 5, wherein said plurality of ridges engage said crown when plate member is secured against said seat portion wit said locking member, said engagement between said ridges and said crown preventing said anchor member from pivoting relative to said coupling member.

7. The system of claim 6, wherein said crown includes a cup portion extending from said seat portion, said cup portion including a receptacle for receiving said head of said anchor member therein.

8. The system of claim 7, wherein said crown includes a through-hole extending through said seat portion and into said receptacle of said cup portion.

9. The system of claim 1, wherein said post includes external threads extending therealong for threadingly receiving said locking member thereabout.

10. The system of claim 9, wherein said locking member includes a body having a wall extending about a central bore for receiving said post, said pall including a slot extending therethrough transversely to said bore in communication with said bore.

11. The system of claim 1, wherein said at least one opening of said plate member includes an elongate slot.

12. The system of claim 11, wherein said plate member includes a rod receiving portion defining a passage extending transversely to said elongate slot, said passage for receiving a rod therethrough.

13. The system of claim 1, wherein said plate member includes an arcuate profile along said upper and lower surfaces.

14. The system of claim 1, wherein said plate member includes a plurality of slots therealong.

15. A spinal plating system, comprising:
    an elongate plate member extending along a longitudinal axis and including at least one opening extending therethrough between an upper surface and an opposite lower surface, said lower surface being positionable toward the spinal column;
    an anchor assembly engageable to said plate member, said anchor assembly including:
    a coupling member including a post positionable trough said at least one opening, said coupling member including a receiver portion positionable along said lower surface of said plate member, said receiver portion including a receptacle opening away from said plate member, wherein said coupling member includes opposite windows opening into said receptacle;
    an anchor member including a head pivotally ca4ured in said receptacle of said receiver portion, said anchor member including a lower portion extending from said head for engaging a bony structure of the spinal column, said anchor member being pivotal relative said plate member and said receiver portion when said post is engaged to said plate member in said at least one opening; and
    a crown positioned in said receptacle of said coupling member in contact with said head of said anchor member, said crown including a heat portion extending through said opposite windows of said coupling member along said lower surface of said plate member, wherein said anchor assembly includes:
    a locking member engageable to said post and positionable in contact with said upper surface of said plate member to secure said lower surface of said plate member in contact with said seat portion of said crown.

16. The system of claim 15, wherein said anchor member is non-pivotally engaged in said receiver portion when said locking member is positioned in contact with said upper surface of said plate member to firmly engage said lower surface of said plate member against said seat portion thereby engaging said crown against said head of said anchor member.

17. The system of claim 16, wherein said crown incl1des a cup portion extending from said seat portion, said cup portion defining a receptacle for receiving said head of said anchor member, said head of said anchor member including a plurality of ridges for engaging said cup portion to non-pivotally secure said anchor member in said coupling member.

18. The system of claim 15, wherein when said locking member is positioned in contact with said upper surface of said plate member to firmly engage said lower surface of said plate member against said seat portion of said crown, said anchor member is pivotal in said coupling member.

19. The system of claim 15, wherein said opening of aid plate member includes at least one slot elongated along said longitudinal axis of said plat member.

20. The system of claim 15, wherein said plate member is curved along said longitudinal axis so that said upper surface is concave and said lower surface is convex.

21. The system of claim 15, wherein said plate member includes a rod receiving portion defining a passage for receiving an elongate rod.

22. The system of claim 21, wherein said at least one opening is an elongated slot extending transversely to said passage.

23. The system of claim 15, wherein said lower portion of said anchor member includes a threaded shaft.

24. The system of claim 23, wherein said anchor member includes a lumen extending from said head through a distal tip of said threaded shaft.

25. The system of claim 24, wherein said head includes a tool engaging recess in communication with said lumen.

26. The system of claim 15, wherein said coupling member includes an internal passage extending axially through said post in communication with said receptacle.

27. The system of claim 26, wherein at least a portion of said passage is configured to engage a driving tool.

28. The system of claim 26, wherein said head of said anchor member includes a tool engaging recess in communication with said receptacle.

29. The system of claim 28, wherein said crown including a through hole alignable with said passage of said coupling member and said tool engaging recess of said anchor member.

30. The system of claim 15, wherein said post is engageable with said plate member so that said coupling member is non-pivotal relative to said plate member.

31. The system of claim 15, wherein said lower portion of said anchor member is a threaded shaft and said anchor member includes an unthreaded neck portion between said head and said threaded shaft.

32. The system of claim 31, further comprising a clip positioned about said neck portion and extending between said coupling member and said head, said clip being sized to prevent passage of said head therethrough to retain said anchor member in said receptacle of said coupling member.

* * * * *